United States Patent
Lal et al.

(10) Patent No.: US 8,197,418 B2
(45) Date of Patent: Jun. 12, 2012

(54) MICROPROBES

(75) Inventors: Amit Lal, Ithaca, NY (US); Darius Paduch, Red Bank, NJ (US); Ramkumar Abhishek, Ithaca, NY (US); Peter Schlegel, Larchmont, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/663,552

(22) PCT Filed: Jun. 9, 2008

(86) PCT No.: PCT/US2008/066375
§ 371 (c)(1),
(2), (4) Date: Aug. 26, 2010

(87) PCT Pub. No.: WO2008/151328
PCT Pub. Date: Dec. 11, 2008

(65) Prior Publication Data
US 2010/0324453 A1    Dec. 23, 2010

Related U.S. Application Data

(60) Provisional application No. 60/942,879, filed on Jun. 8, 2007.

(51) Int. Cl.
*A61B 5/00* (2006.01)
*A61B 5/103* (2006.01)
*A61B 5/117* (2006.01)
(52) U.S. Cl. .............................. 600/552; 600/587
(58) Field of Classification Search ............ 600/552, 600/553, 561, 587; 604/65–67; 606/169; 438/10, 11, 17, 18, 50
See application file for complete search history.

(56) References Cited

U.S. PATENT DOCUMENTS

| | | | |
|---|---|---|---|
| 5,728,089 A | 3/1998 | Lal et al. | |
| 6,010,461 A | 1/2000 | Haniff et al. | |
| 6,638,249 B1 * | 10/2003 | Lal et al. | 604/151 |
| 6,740,058 B2 * | 5/2004 | Lal et al. | 604/65 |
| 7,927,288 B2 * | 4/2011 | Gianchandani et al. | 600/561 |

OTHER PUBLICATIONS

International Search Report and Written Opinion of the International Searching Authority for PCT/US2008/066375 mailed Jan. 23, 2009 (6 pp.).
Chen, Xi et al., "Ultrasonically Actuated Silicon Microprobes for Cardiac Signal Recording," IEEE Transactions on Biomedical Engineering, vol. 53(8):1665-1671, Aug. 2006.
DiMaio, S.P. et al., "Needle Insertion Modelling and Simulation," Proceedings of the 2002 IEEE International Conference on Robotics & Automation Washington, DC, pp. 2098-2105, May 2002.
Najafi K. et al., "A High-Yield IC-Compatible Multichannel Recording Array," IEEE Transactions on Electron Devices, vol. ED-32(7):1206-1211, Jul. 1985.
Okamura A.M. et al., "Force Modeling for Needle Insertion Into Soft Tissue," IEEE Transactions on Biomedical Engineering, vol. 51(10):1707-1716, Oct. 2004.
Piefke F., "Chord Length Distribution of the Ellipse," Lithuanian Mathematical Journal, vol. 19(3):325-333, 1979.
Schlegel, P.N., "Testicular Sperm Extraction: Microdissection Improves Sperm Yield with Minimal Tissue Excision," vol. 14(1):131-135, Jan. 1999.

* cited by examiner

*Primary Examiner* — Max Hindenburg
*Assistant Examiner* — Devin Henson
(74) *Attorney, Agent, or Firm* — Perkins Coie LLP (57) ABSTRACT

Microprobes in various designs are provided including microprobes having a bulk base and a thin probe extending from the bulk base and a Wheatstone-bridge sensor circuit for measuring strain in the thin probe, and microprobes with two thin probes extending from the bulk base with their respective integrated Wheatstone-bridges to eliminate common mode forces experienced by the two thin probes.

31 Claims, 8 Drawing Sheets

MICROPROBES

CROSS-REFERENCE TO RELATED APPLICATION

This application claims the benefit of U.S. Provisional Application No. 60/942,879, filed Jun. 8, 2007, the contents of which are hereby incorporated herein by reference.

STATEMENT REGARDING FEDERALLY SPONSORED RESEARCH OR DEVELOPMENT

This invention was made with government support under Grant No. RL073644 awarded by the National Institutes of Health and and/or DARPA Grant No. N66001-07-12019 awarded by DARPA. The Government has certain rights in this invention.

DETAILED DESCRIPTION

In medical procedures such as percutaneous liver biopsy and tactile tissue characterization during endoscopic surgery, force measurement during the tissue-tool interaction is important [1-2]. By monitoring the reactive force between the tissue and the surgical tool, information about the internal structure of the tissue can be revealed.

Microdissection testicular sperm extraction (TESE) is a highly invasive surgical procedure in which tubules carrying fertile spermatazoa are surgically extracted from the testicle of an infertile male, by visual examination of the seminiferous tubules of the testicle under a microscope [3]. Tubules with low spermatogenesis have thinner walls and smaller diameter, as compared to healthy tubules. By monitoring the force experienced by a microfabricated force probe inserted with 100-micron-scale incision, the surgeon can map the diameter and stiffness of tubule walls encountered during the incision. This could eliminate the need for a large incision and postoperative care, microscope visualization, excision of large volumes of testicular tissue, and reduces risks of causing permanent damage to the testis.

Thin-beam silicon microprobes have been used for electrical activity recording in neural tissues [4]. They provide high spatial resolution, reduced tissue damage and easy integration with microelectronics. Silicon microprobes for tissue characterization in surgery are especially favorable due to the potential of integrating a variety of sensors. Previously, our group has demonstrated reduction in penetration force of canine cardiac tissue, by using silicon microprobes integrated with PZT (piezoelectric) ultrasonic actuator, with electrodes to measure action potentials [5]. Here we demonstrate tubule dimension measurement inside rat testis tissue by insertion of silicon microprobes with integrated Wheatstone-bridges formed by polysilicon strain gauges (circuit diagram in FIG. 7). Two silicon microprobes 110 and 120 with strain gauges are fabricated on the device to eliminate common mode forces experienced by the two probes 110 and 120. The tubule diameter measurement resolution of ±10 μm is sufficient to distinguish between tubules carrying fertile or infertile sperm.

1. Device Fabrication and Experimental Procedure

The design and fabrication of the microprobe is similar to the ultrasonic microprobes reported earlier [5], with dimensions of the microprobes altered to improve sensitivity for tissue more delicate than cardiac tissue, and further modifications described below.

The microprobe described in [5] included two probe bodies extending from a base for the purpose of improving mechanical stability during tissue insertion compared to a microprobe having one probe extending from a body. The inventors here have discovered that the presence of two probe bodies in close proximity offers another advantage: they can be used to eliminate common mode noise from the microprobe signals. To do so, the microprobes are formed sufficiently close to one another that they are in the same tissue milieu when inserted (and thereby subject to the same systemic noise) but far enough apart to minimize the chance that both probes are touching the same structure. In this manner, one probe can be expected to be touching a structure while the other probe can be expected to be reading the systemic noise. The signal from the first probe, therefore, can be cleaned of the systemic noise by subtracting from it the signal of the second probe.

The inventors here have also discovered that an unexpected and surprising artifact of the fabrication procedure of the microprobe in [5] permits higher spatial resolution of the microprobe with no added fabrication steps. Specifically, the etching process results in the creating of two blades on the probe body, not the single blade that was expected. The two blades may obtain spatially close but distinct sensor data. Moreover, sensor data based on tension/compression in the probe body may be obtained for the two blades using a single sensor construct, as described below in greater detail.

Figure 1:
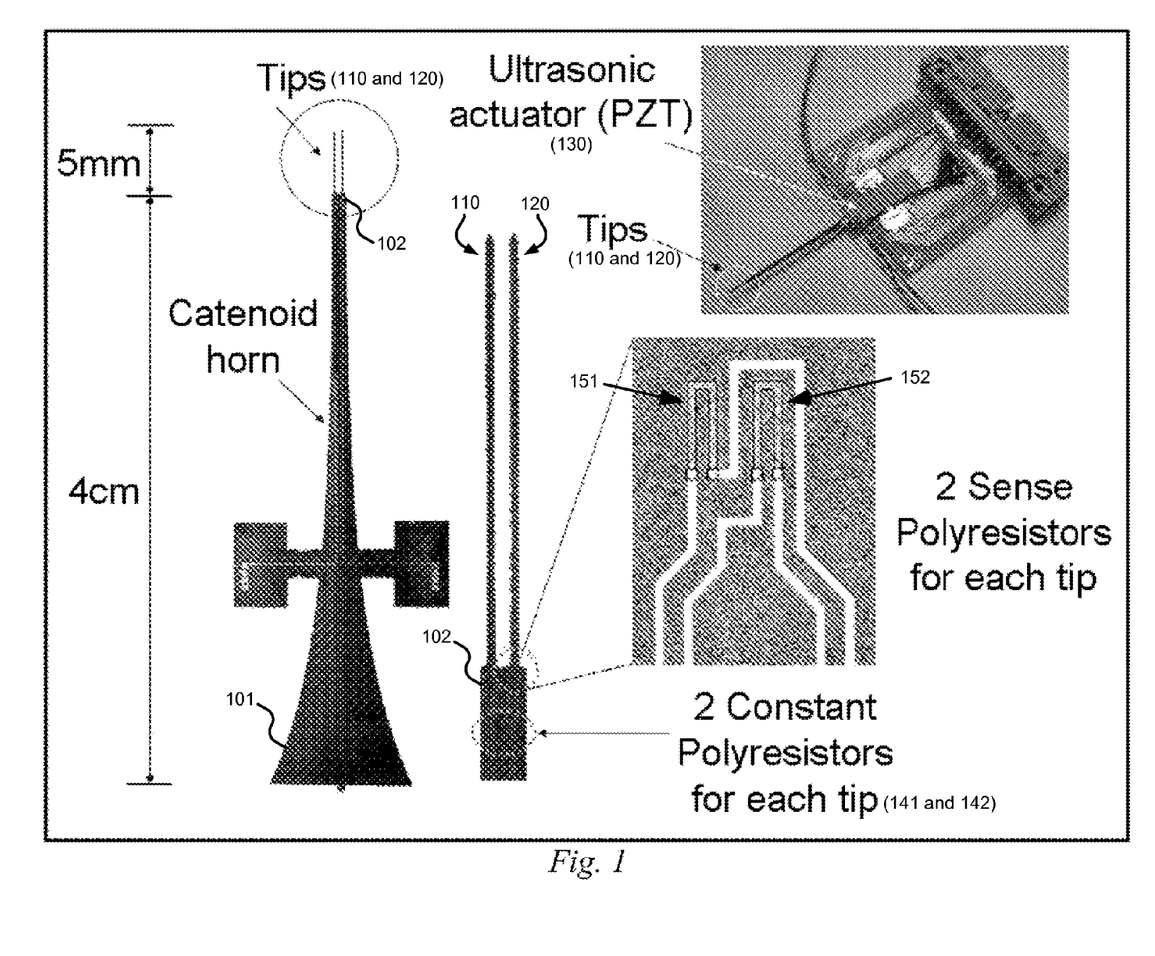
FIG. 1: Optical photograph of the fabricated device. The microprobes integrated at the tip of the silicon ultrasonic catenoid horn are 5 mm long, 100 μm wide and 140 μm thick, and 0.5 mm apart.
Figure 2:
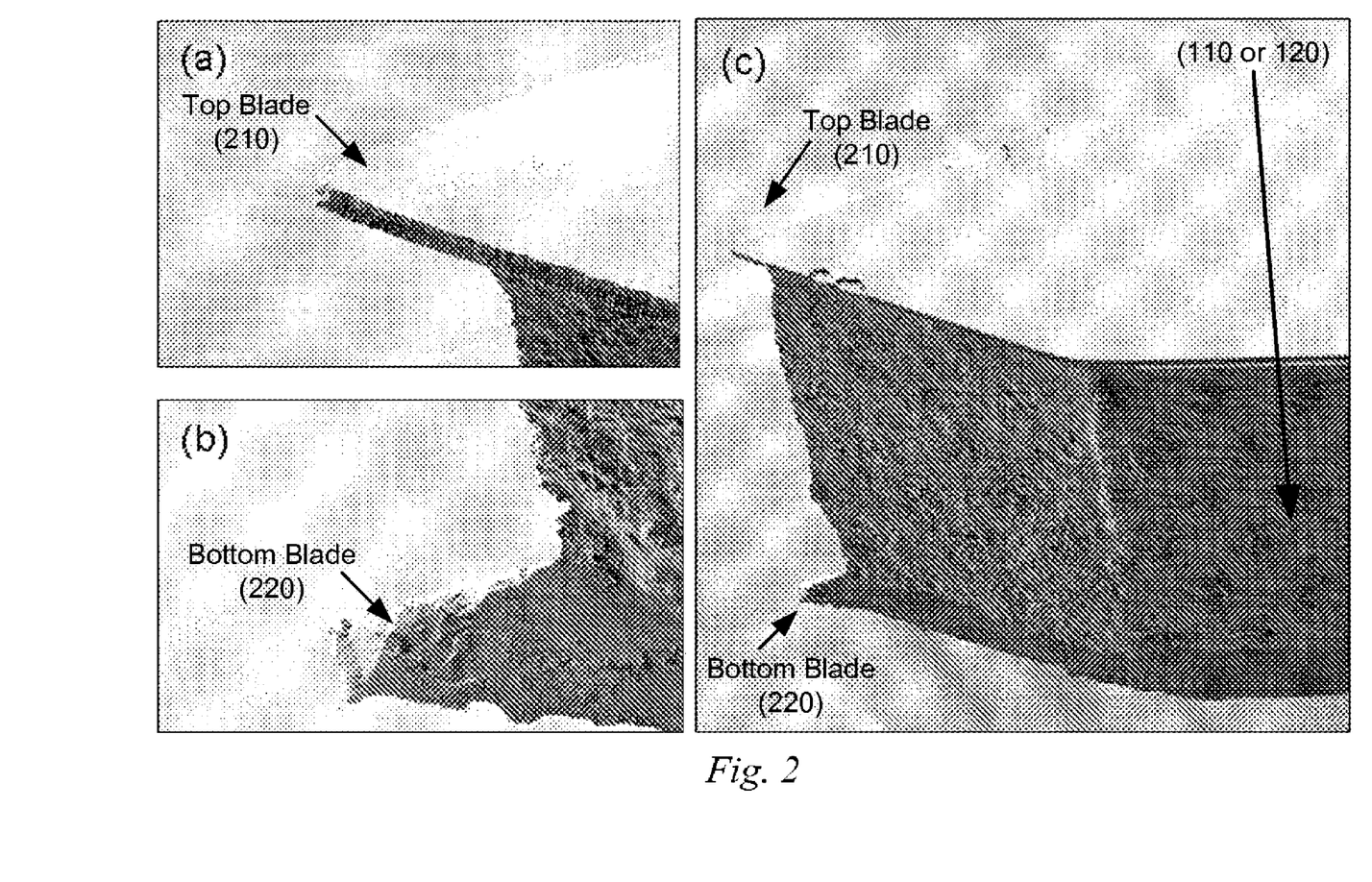
FIGS. 2A-C: SEM images of (a) Silicon nitride blade on top (scale is 10 μm), (b) Silicon blade at the bottom (scale is 10 μm) and (c) both blades on the microprobe (scale is 20 μm).
Figure 7:
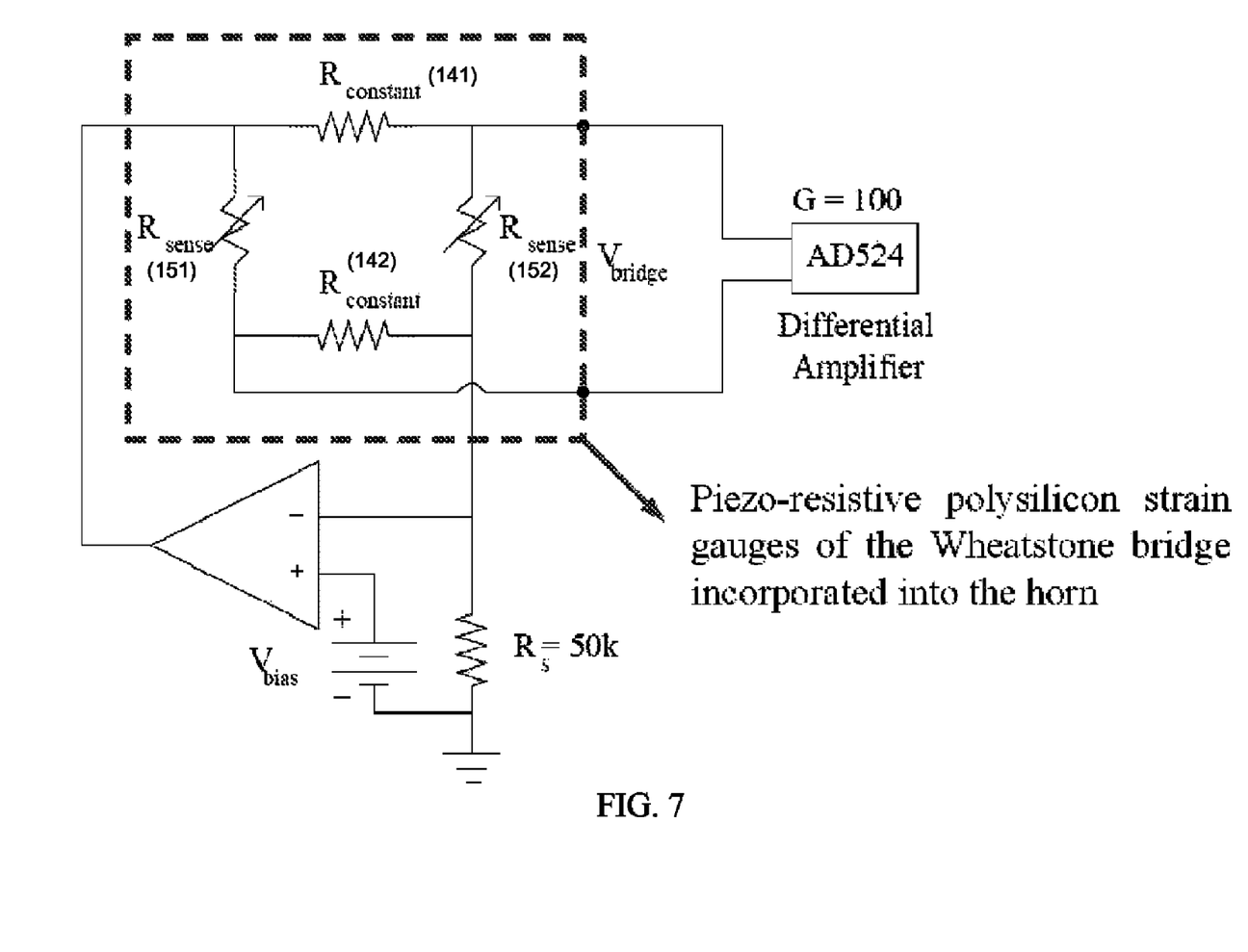
FIG. 7: Wheatstone bridge strain gauge.
Figure 8:
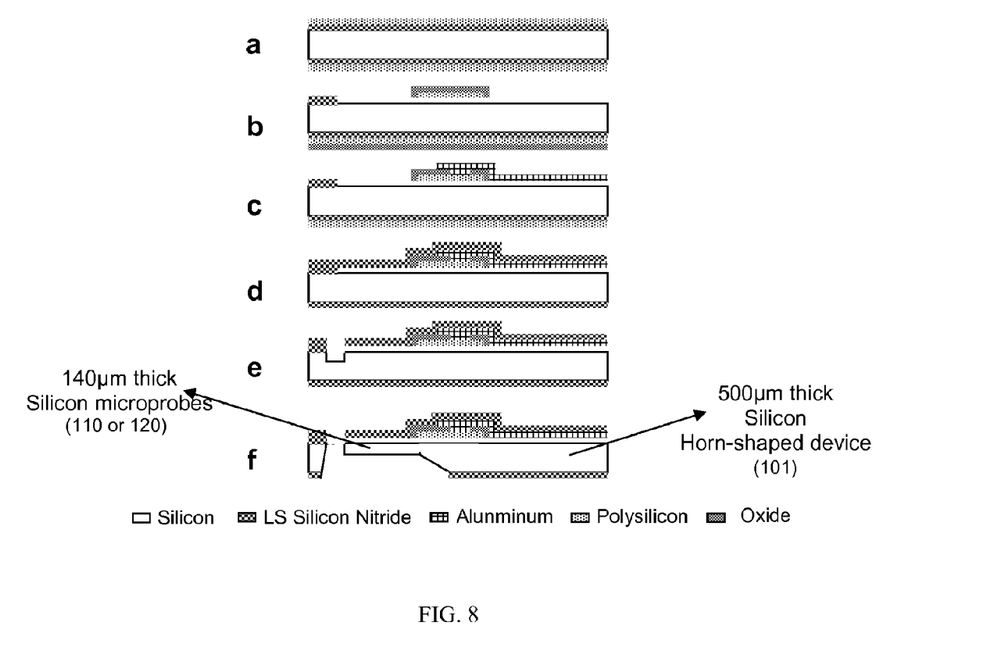
FIGS. 8A-F: Fabrication technique.

The dimensions of the probe bodies 110 and 120 here were selected to provide force sensitivity in the appropriate range for sensing impingement on seminiferous tubules; accordingly the silicon microprobes 110 and 120 were 5 mm long, 100 μm long wide and 140 μm thick projecting outwards at the tip 102 of the horn 101 (FIG. 1). The catenoid shape of the horn 101 in conjunction with the ultrasonic actuator 130 gives an added advantage of reducing tissue damage during incision. A further modification to the previously reported silicon microprobe is the addition of a sensor construct in the form of set of four polysilicon resistors 141, 142, 151 and 152 forming a Wheatstone bridge arrangement for each of the two tips 110 and 120 as shown in FIG. 7. (The microprobe in [5] merely included electrodes for measuring cardiac electropotentials) The tip of each of the microprobes 110 and 120 has 2 sharp blade-like edges 210 and 220—a V-shaped edge 210 on the top formed by the LPCVD nitride film and one 220 at the bottom formed by silicon due to the anisotropic backside-only KOH etch (FIG. 2). A protocol for preparing the probe 110 or 120 is provided below and shown in FIG. 8. The bottom blade/edge 220 resulted unexpectedly from undercutting during the backside-only KOH etch; the V-shaped edge 220 provided a geometry that favored KOH etching into the (1,1,1) plane of the silicon wafer, thereby creating the blade-like edge shown in FIG. 2b.

The polysilicon strain gauges (~10KΩ, the resistance of which changes with the strain experienced, are positioned to sense the compressive strain generated when the microprobe 110 or 120 encounters the seminiferous tubules. On both the microprobes 110 and 120, two (constant) polysilicon resistors 141 and 142 are positioned on the bulk nearly constant with respect to the strain experienced by the microprobe 110 or 120. The other two (sense) polysilicon resistors 151 and 152 are positioned on the microprobe 110 or 120 near its clamped edge 102, so their resistance changes with the compressive/tensile strain experienced when the blade-like edges of microprobes 110 and 120 pierce the tubule walls (FIG. 1). Temperature sensitivity of the piezoresistors 151 and 152 can be compensated by laser trimming or active signal processing using temperature sensor integrated on the microprobes 110 and 120. The microprobes 110 and 120 are inserted into the tissue using a μ-manipulator with 0.2 μm precision (MP-285, Sutter Instruments Inc.). The polysilicon resistors 141, 142, 151 and 152 on the microprobe 110 or 120 forming a Wheatstone bridge are connected in a constant current configuration and the bridge voltage is amplified by an instrumentation amplifier (AD524).

2. Force Characterization

To measure the force sensitivity of the strain gauge the microprobe was clamped to a μ-manipulator and placed in the way of a force gauge clamped to a stage. When the tubules are encountered by the blades on the microprobe, the strain experienced by the polysilicon resistors is due to a combination of pure axial compression and the bending of the cantilever. Depending on whether the tubules are encountered by the top or bottom blade, the bending moment causes a compressive or tensile strain respectively. The sensitivity of the strain gauge to pure axial compressive (0.2V/N) and, compressive and bending moments (0.259V/N) is experimentally measured by moving the microprobe against the force gauge along the axis of probe, and perpendicular to it. The strain due to the bending moment of a force experienced by the blade, along the edge of the microprobe, is calculated to be 3 times the pure axial compressive stress. Therefore the sensitivity of the top gauge can be estimated as $(-0.2+3\times(-0.259))=-0.977$V/N. The sensitivity for the bottom blade can be assumed to be purely due to the bending moment of the force, since the force applied axially is far away from the strain gauge layer on the microprobe (i.e. $3\times0.259=0.577$V/N). The sensitivities were measured with amplification of $G=100$.

3. Testicular Tubule Assay

Figure 3:
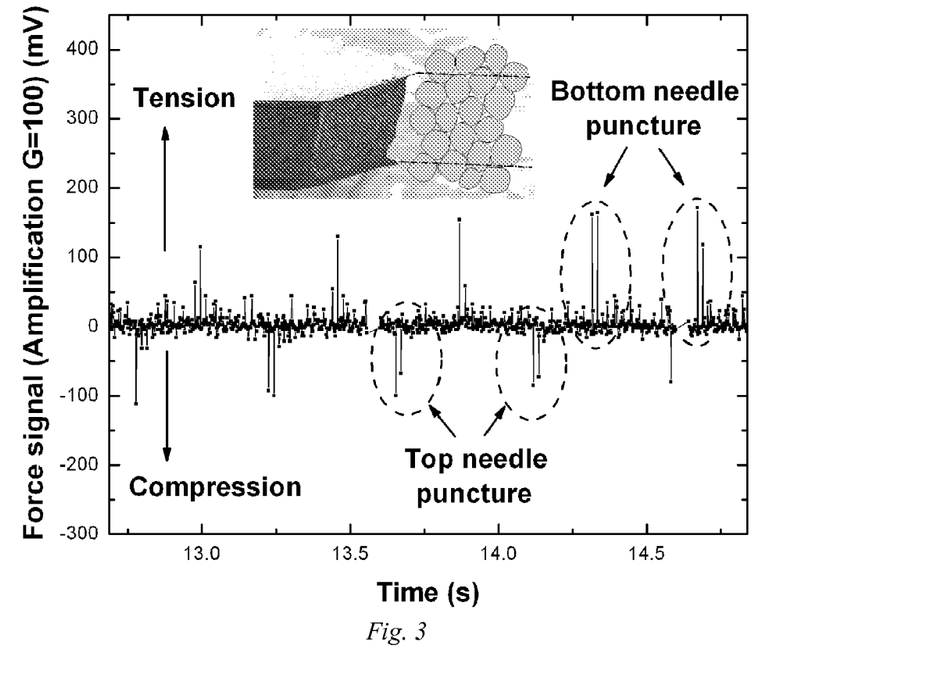
FIG. 3: Detection of tubules (sensed force signal vs. time) in rat testis tissue by penetration with microprobe at a constant velocity of 100 μm/s. Cross-sectional view of microprobe penetrating the tubules is also shown with correct scale factor.
Figure 4:
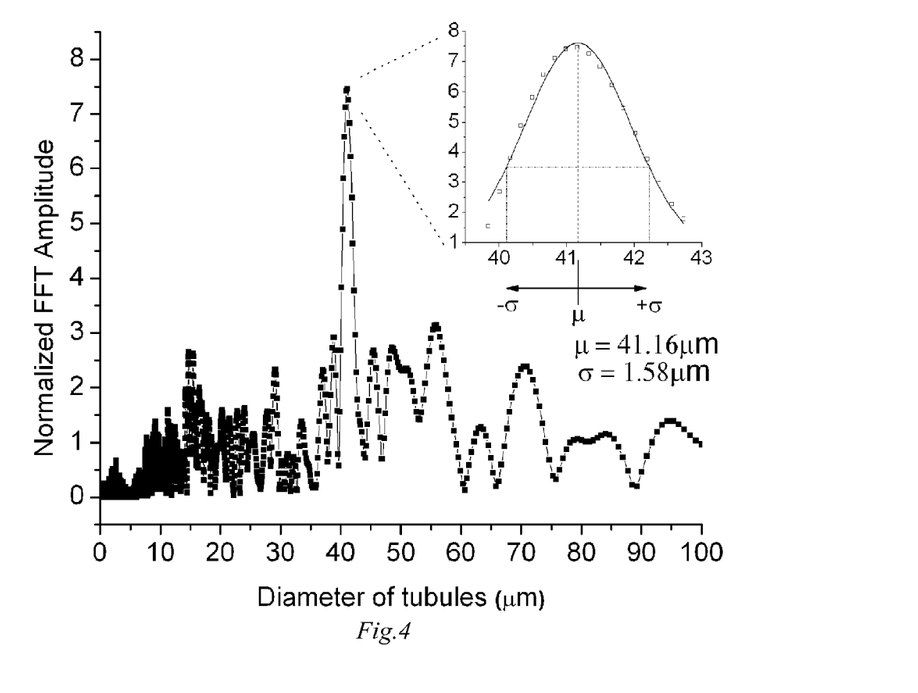
FIG. 4: Normalized FFT amplitude of the time-domain force signal, with frequency modified to diameter of tubules sensed (x-axis), which is given by 100 μm/s*[1/frequency].

The microprobes are inserted into the rat testis tissue to a depth of 2 mm at 100 m/s. The bulk portion of the microprobe is intended to be thicker in order to be stiff enough to be used for penetrating the outer testicular tissue and eventually reaching the seminiferous tubules. Once inside the tissue, the blades on the microprobe puncture the tubules and the puncture artifact in the force signal is observed to be a negative spike (compression) for the top nitride blade and a positive spike (tension) for the bottom silicon blade (FIG. 3). The average time between 2 consecutive puncture artifacts multiplied by the speed (100 μm/s) can be taken as the mean diameter of the tubules, since the tubules are densely packed wall-to-wall in the tissue. From the FFT of the positive and negative spike data, the effective tubule diameter was calculated to be $41.16\pm1.58$ μm (FIG. 4). This is close to the expected tubule diameter of rat testis.

Figure 5:
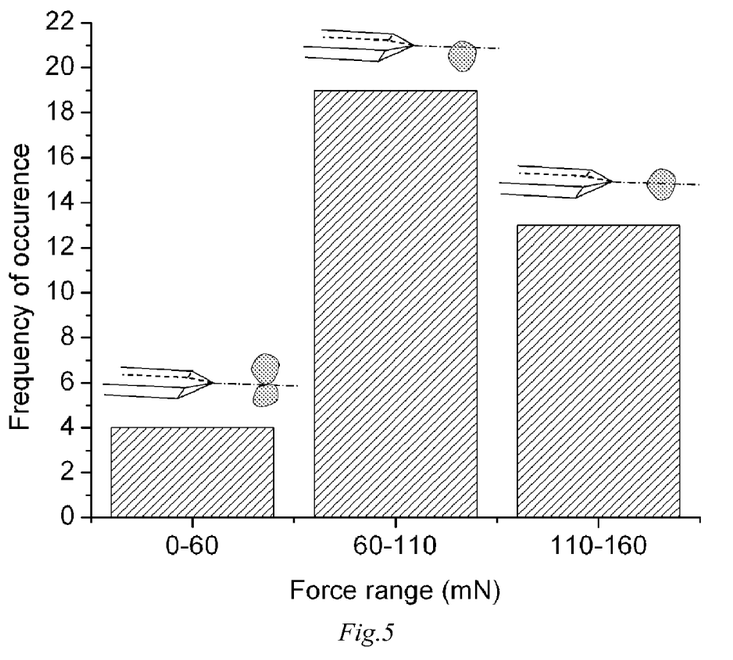
FIG. 5: Relative frequency of occurrence of tubule puncture events corresponding to different insertion forces suggest that cuts are made into tubules or between tubules.

The mean puncture force for the tubule wall as seen by the top blade on the microprobe was observed to be 101.51 mN. The data was also analyzed by amplitude binning (FIG. 5), which indicates that the punctures were probably of three kinds—a) either puncturing through the walls along the diameter (110-160 mN) or b) along any chord of the tubule's cross-section (60-110 mN) or c) separating attached tubules (0-60 mN). Thus we can quantify the size and the stiffness of the tubules encountered during an insertion experiment.

Figure 6:
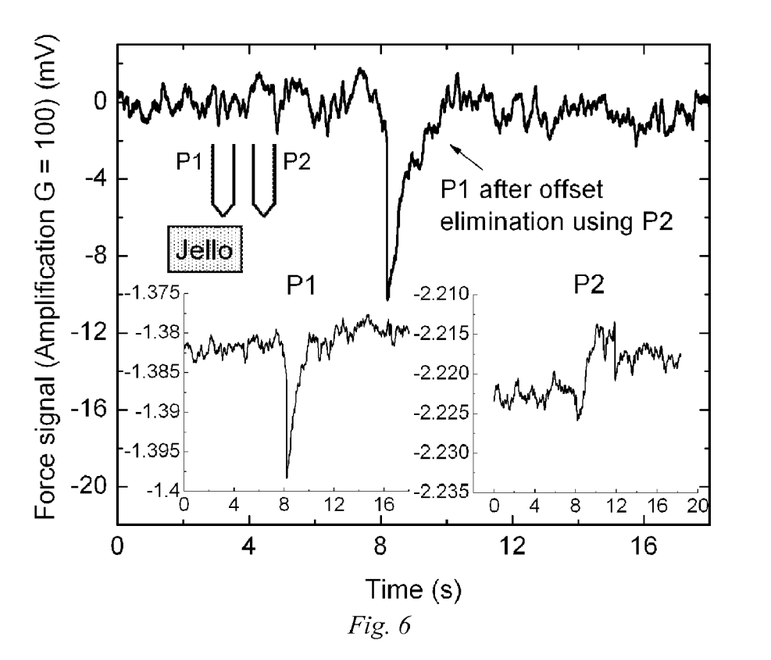
FIG. 6: Offset elimination in signal using offset of the $2^{nd}$ probe, when one probe pierces a block of gelatin and the other does not.

Since the two microprobes on the device are separated by a distance of 500 μm, the probability that both the microprobes will be cutting tubules at the same time is small. By monitoring the ratio of the offsets in the Wheatstone bridge of the strain gauges in the 2 microprobes when both are not cutting, the offset of a probe when cutting a tubule can be eliminated if the other probe is not encountering any tubules. A controlled experiment was performed in which only one of the 2 probes was allowed to pierce a gelatin block. The offset of the probe piercing the gelatin was eliminated by using the recorded ratio of the offsets initially before penetration and the offset of the non-piercing probe (FIG. 6). This method can also help remove other effects such as drift, loading, temperature etc.

4. Tubule Measurement

Figure 9:
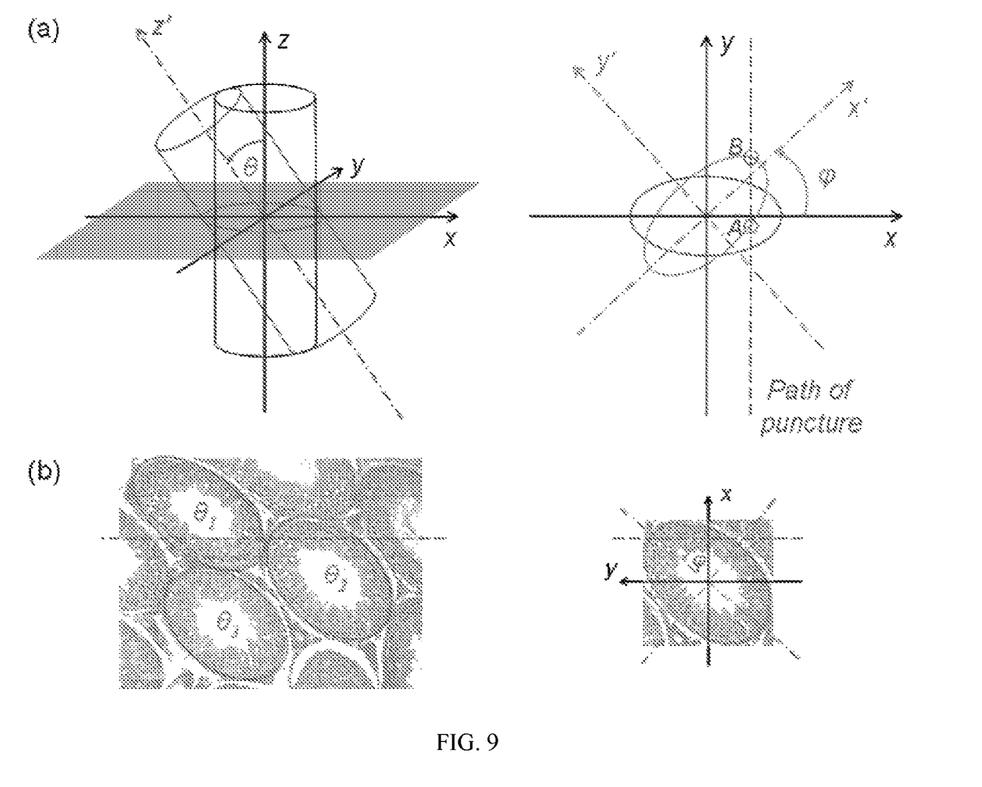
FIGS. 9A-B: (a) Random orientation of tubule defined by angles θ and φ, being encountered by the microprobe (path of puncture of the blade) and size measured by microprobe=AB and (b) histology slide of seminiferous tubules showing elliptical cross-sections of the tubules and depiction of the path of puncture through the tubule.
Figure 10:
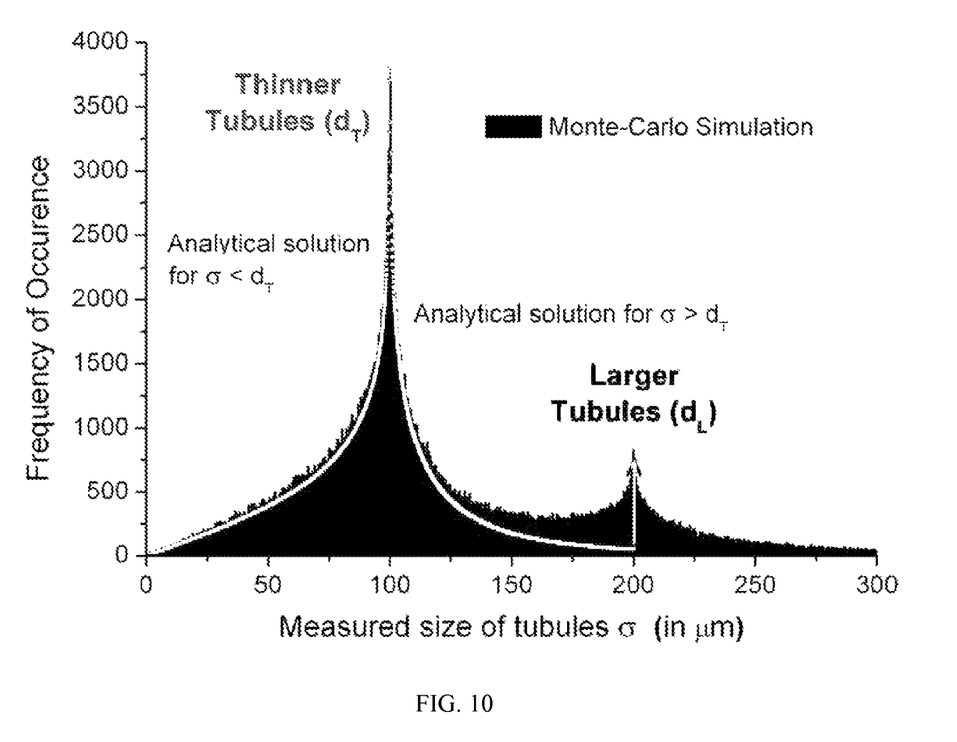
FIG. 10: Binning of simulated (Monte-Carlo) sizes measured by microprobe assuming the presence of mostly thinner ($d_T$) and few larger ($d_L$) tubules. Observed frequency of occurrence being greater than the analytically expected value (corresponding to the thinner tubule diameter) at $\phi=d_L$, helps validate the presence of larger tubules.

Knowledge of the probability distribution of sizes measured by the microprobe when inserted in tissue permits calculation of the average diameter of the tubules in the tissue. Monte-Carlo simulations are done by randomizing the orientation of the tubules (with constant diameter) and the length of the path of puncture through the tubule (length AB in FIG. 9A) is measured, which corresponds to the size measured by the microprobe. The following assumptions are made in the simulation—

Tubules are assumed to be closely packed right-circular cylinders with fixed diameter and height much greater than the thickness of the microprobe (140 μm).

Path of puncture is assumed to be a line with width and height (of the blade, in our case) much less than the diameter of the tubule. The puncture is assumed to be ideal with no compression artifact.

Penetration through successive cylinders is modeled by randomizing the orientation of the tubule. The angles $\phi$ and $\theta$ are randomly varied with uniform and $\sin(\theta)\times\cos(\theta)$ distributions respectively [6].

The Monte-Carlo simulation shows that the maximum probability of occurrence corresponds to a measured size equal to the diameter of the tubule. This explains the reason for the FFT of the force vs. time curve (FIG. 4) peaking around 40 μm, which is close to the average tubule diameter in the tissue. Thus by noting the measured size which has the maximum occurrence in multiple probing experiments, the surgeon can have an estimate of the average tubule diameter in the region of interest.

$$f(\sigma, d) = \int_{\theta_o}^{\frac{\pi}{2}} \sin\theta \cos\theta \left( \int_0^{\varphi_o} \sqrt{\frac{(1-(\sin\theta\sin\varphi)^2)^2}{1-\left(\frac{\sigma}{d}\right)^2(1-(\sin\theta\sin\varphi)^2)}} \cdot d\varphi \right) \cdot d\theta \quad (1)$$

where $\sigma < d$: $\varphi_o = \frac{\pi}{2}$ and $\theta_o = 0$ $\sigma > d$: $\varphi_o = \arcsin\left(\frac{\sqrt{\sigma^2-d^2}}{\sigma \sin\theta}\right)$ and $\theta_o = \arccos\left(\frac{d}{\sigma}\right)$ Analytical expression for the probability distribution of measured sizes, is derived for a given diameter of the tubule [7] (say, 100 μm) and is observed to fit the Monte-Carlo simulations. The analytical expression for the probability distribution for a measured size (σ) and fixed tubule diameter (d) is as follows—

In the practical scenario, the surgeon is primarily interested in locating regions in the testis with sperm production, wherein the tubules are larger in diameter, and biopsy of tubules in that region for sperm extraction. Since the tubules with larger diameter (sites of sperm production) in the testes of the patient are very few and are sparsely located, they can be assumed to be embedded in a mass of smaller diameter tubules which occupy the major portion of the testes. Knowledge about the probability distribution of measured sizes will help the surgeon ascertain the presence of larger fertile tubules embedded in a mass of thinner infertile tubules.

Assuming a large set of sizes measured by probing multiple locations in a region of interest, if the tissue contains few larger-diameter tubules embedded in a mass of smaller-diameter tubules then two peaks corresponding to the diameter of the smaller- and larger-diameter tubules is expected when the measured sizes are binned. The peak for the smaller-diameter tubules is higher in magnitude than that of the larger tubules because of fewer large tubules, as seen in the Monte-Carlo simulation results in FIG. 2. If the observed frequency of occurrence at measured size equal to the larger tubule diameter (i.e. $\sigma=d_L$), is greater than the value calculated by using the analytical expression (1) corresponding to the smaller tubule diameter (i.e. $f(\sigma=d_L, d_T)$), then the presence of larger tubules in the tissue is confirmed (FIG. 2). Thus by sufficient sampling of tubules by the microprobe in a given region of interest, the surgeon can identify the presence of healthy tubules by using the analytical expression for the probability of occurrence of measured sizes. To further validate the presence of larger tubules, the analytical expression (1) for probability distribution of measured sizes corresponding to smaller and larger tubules (i.e. $f(\sigma, d_T)+f(\sigma, d_L)$), can be used to fit the frequency of occurrence of measured sizes.

5. Use by Surgeon:

The Instrument—The final product is envisioned to be a hand-held device with the silicon horn and the microprobes/tips mounted on a controlled 3-axis motion stage. The surgeon, after cutting open the scrotum to expose the area under which tubules are present, will position the hand-held device on the tissue with, say, a suction cup around the microprobes; the microprobes are not yet in contact with the tissue. The motion stage will be programmed for x-y motion in order to move the microprobes/tips to the desired position of incision (within the region under the suction cup), and the z-motion for insertion of the microprobes/tips into the tissue at a constant velocity.

The Procedure—Once the surgeon positions the hand-held device at a particular region to be probed, the surgeon will press a button on the device which triggers the stage for insertion of the microprobes/tips into the tissue and record sizes of the tubules at the current location of the microprobes/tips. The stage then positions the microprobes in locations corresponding to a grid, say 25 locations in a 5 mm×5 mm area within the region under the suction cup, inserting the microprobes/tips at every location and recording the sizes of the tubules encountered.

The User-Interface—The device is connected to a black-box which contains a data-acquisition system which records the force signals and data-processing hardware which deciphers the average diameter of the tubules and, the existence and diameter of larger tubules in the region if any. The results obtained are displayed on an LCD screen on the black-box. The display on the LCD screen corresponding to the 2 cases, namely a) larger-diameter tubules FOUND and b) larger-diameter tubules NOT FOUND, are discussed as follows— a) Larger-diameter tubules FOUND

The LCD screen may a suitable message, e.g.:
FOUND LARGER-DIAMETER TUBULES
Average size of Smaller-diameter tubules–<_>μm
Average size of Larger-diameter tubules–<_>μm
b) Larger-diameter tubules NOT FOUND
The LCD screen may display a suitable message, e.g.:
LARGER-DIAMETER TUBULES NOT FOUND
Average size of Smaller-diameter tubules–<_>μm In case (a), the average size of larger-diameter tubules is also displayed so that the surgeon can confirm that the difference in size as compared to the smaller-diameter tubules is significant enough to expect sperm production.

6. Protocol for preparing probe (starting with (1,0,0) silicon)

1) MOS Clean: Clean wafers of all organic material on surface in preparation for Nitride deposition.

2) MOS Furnace:
Deposit LPCVD (Low Pressure Chemical Vapour Deposition) Low Stress Silicon Nitride layer (1 μm) (LS Silicon Nitride)
Undoped Polysilicon layer (1 μm)
Ion implantation of Polysilicon with Boron
3) Patterning Polysilicon to form 'U' shaped resistors
Spin Photoresist—S1827 at 3000 rpm @ 1000 rpm/s for 30 seconds
Bake at 115 C for 3 minutes
Expose Photoresist with mask containing Polysilicon resistors Pattern using Contact Aligner tool (EV620)
Develop for 2 minutes using MIF 300 developer solution
Descum the trenches by using Oxygen plasma for 30 seconds
Etch 1 μm Polysilicon using $SF_6+O_2$ chemistry for 3 minutes using Reactive Ion Etching (RIE) tool (Oxford 80 #1/2)
Strip the PR by rinsing with Acetone and then with IPA to remove acetone drying residues
4) MOS Furnace:
Grow thermal oxide on polysilicon (300 nm)
5) Patterning Oxide grown on top of Polysilicon resistors to open holes for contact with Aluminum
Spin Photoresist—S1827 at 3000 rpm @ 1000 rpm/s for 30 seconds
Bake at 115 C for 3 minutes Expose Photoresist with mask containing Contact Holes Pattern using Contact Aligner tool (EV620)

Develop for 2 minutes using MIF 300 developer solution

Descum the trenches by using Oxygen plasma for 30 seconds (Aura 1000)

Wet Etch 300 nm of Oxide using 6:1 Buffered Oxide Etch (BOE) solution containing mainly HF Strip the PR by rinsing with Acetone and then with IPA to remove acetone drying residues 6) Sputtering and Patterning Aluminum metal lines Sputter 600 nm of Aluminum+1% Silicon. Aluminum+1% Silicon is used to get an ohmic contact between the metal and polysilicon Spin Photoresist—S1827 at 3000 rpm @ 1000 rpm/s for 30 seconds Bake at 115 C for 3 minutes Expose Photoresist with mask containing Metal lines Pattern using Contact Aligner tool (EV620)

Develop for 2 minutes using MIF 300 developer solution

Descum the trenches by using Oxygen plasma for 30 seconds

Wet Etch 600 nm Aluminum using Aluminum Etchant (Phosphoric acid, Nitric acid, Acetic acid and water) heated to 6° C. for 15 minutes Strip the PR by rinsing with Acetone and then with IPA to remove acetone drying residues 7) Deposition and Patterning of PECVD (Plasma Enhanced Chemical Vapour Deposition) of LS (Low Stress) Silicon Nitride—Passivation patterning Deposit 1 μm of LS Silicon Nitride for passivating/protecting the metal lines from possible contamination Spin Photoresist—S1827 at 3000 rpm @ 1000 rpm/s for 30 seconds Bake at 115 C for 3 minutes Expose Photoresist with mask containing Metal Pad opening for wire-bonding to external circuit Pattern using Contact Aligner tool (EV620)

Develop for 2 minutes using MIF 300 developer solution

Descum the trenches by using Oxygen plasma for 30 seconds

Etch 1 μm LS Silicon Nitride using $CHF_3+O_2$ chemistry for 15 minutes using RIE tool (Oxford 80 #1/2)

Strip the PR by rinsing with Acetone and then with IPA to remove acetone drying residues 8) Patterning the horn-shaped device pattern on the BACKSIDE for backside KOH Silicon etching Spin Photoresist—S1827 at 3000 rpm @ 1000 rpm/s for 30 seconds Bake at 115 C for 3 minutes Expose Photoresist with mask containing Horn-shaped backside probe Pattern using Contact Aligner tool (EV620)

Develop for 2 minutes using MIF 300 developer solution

Descum the trenches by using Oxygen plasma for 30 seconds

Etch 1 μm LPCVD LS Silicon Nitride down to the Silicon using $CHF_3+O_2$ chemistry for 35 minutes using RIE tool (Oxford 80 #1/2)

Strip the PR by rinsing with Acetone and then with IPA to remove acetone drying residues 9) Patterning the Horn-shaped device and microprobes pattern on the FRONTSIDE Spin Photoresist—S1827 at 3000 rpm @ 1000 rpm/s for 30 seconds Bake at 115 C for 3 minutes Expose Photoresist with mask containing Horn-shaped frontside along with microprobes Pattern using Contact Aligner tool (EV620)

Develop for 2 minutes using MIF 300 developer solution

Descum the trenches by using Oxygen plasma for 30 seconds

Etch 1 μm PECVD LS Silicon Nitride+1 μm LPCVD LS Silicon Nitride down to the Silicon using $CHF_3+O_2$ chemistry for 50 minutes using RIE tool (Oxford 80 #1/2)

Etch the Silicon down for 140 μm using Deep Reactive Ion Etching (Deep-RIE)

Strip the PR by rinsing with Acetone and then with IPA to remove acetone drying residues 10) Backside-only Silicon Etching using 30% KOH Solution @ 80 C Secure silicon wafer with backside facing out in the single-side silicon etch holder Immerse in 30% KOH Solution @ 80 C with 400 rpm rotation for 7.5 hours (this etching rate, etch concentration, and temperate indicate that the starting material was (1,0,0) silicon.

7. Other applications of technology

A conduit, such as a microchannel, may be built into the device, as described in U.S. Pat. No. 5,728,089, hereby incorporated herein by reference, to permit suctioning of tissue (for sampling or removal), or instillation of substances into the tissue.

The device including the microchannel may be used to extract viable sperm.

The device may be used to detect tissue changes. Cancer is a disease characterized by disorderly division of cells, combined with the malignant behavior of these cells. Malignant cancer cells tend to spread, either by direct growth into adjacent tissue through invasion, or by implantation into distant sites by metastasis. Cancerous tissue is likely to have different properties from the tissue from which it arises. These properties can make tumors detectable using medical imaging technologies, such as ultrasound, MR, or CT.

Techniques have recently been developed to use ultrasound to detect cancerous lesions. These techniques sometimes go under the rubric of "elastography," as the property being measured is tissues' reflectance or absorbance of ultrasound waves, which in turn depends in part on the stiffness of the tissue at hand. For example, ultrasound elastographic techniques have been under development for breast cancer and to detect glaucoma.

The force-measuring silicon microprobe under consideration in this disclosure could also be used to detect differences in the resistance of tissue to the penetration of the probe. These differences may be catalogued and used as baselines to diagnose cancerous tissue and other abnormalities.

The device may also be used in a robotic surgical arm to provide sensor feedback.

8. Alternatives

Microprobes can be made from a variety of materials, including titanium plates, silicon oxide, silicon carbide, sapphire, glass, and varioud low-pressure chemical vapor deposited (LPCVD) materials. The material can be etched or machined (e.g., by using micromachining, laser, electrical discharge machining, etc).

Sensors formed on the probes can include those that sense strain, change in biological impedance, change in temperature, etc.

The microprobe can be used to measure ultrasonic strain on the probe body, to serve as a feedback to optimize piezoelectric actuation parameters.

The microprobe can be used to measure elasticity of structure(s), membrane(s) etc. in contact with the probe core, lower blade or the upper blade.

The microprobe can be actuated at ultrasonic frequencies to cause pressure wave fronts to be generated in a material, to characterize the environment (such as sensing variation in density, viscosity, etc.) in contact with or in the proximity of the probe core, lower blade and/or the upper blade.

Anisotropic etchants other than KOH may be used, such as Ethylenediamine pyrocatechol (EDP), Tetramethylammonium hydroxide (TMAH), sodium hydroxide, lithium hydroxide, cesium hydroxide (CsOH) solution, and hydrazine.

9. References

[1] S. P. Dimaio and S. E. Sacudean, "Needle insertion modeling and simulation," *Proceedings of the IEEE International Conference on Robotics and Automation*, pp. 2098-2105, 2002.

[2] A. M. Okamura, C. Simone, and M. D. O'Leary, "Force modeling for needle insertion into soft tissue," *IEEE Trans. Biomed. Eng.*, vol. 51, no. 10, pp. 1707-1716, October 2004.

[3] P. N. Schlegel, "Testicular sperm extraction: microdissection improves sperm yield with minimal tissue excision," *Human Reproduction*, vol. 14, no. 1, pp. 131-135, January 1999.

[4] K. Najafi, K. D. Wise, and T. Mochizuki, "A high-yield IC-compatible multichannel recording array," *IEEE Trans. Electron Devices*, vol. ED-32, no. 7, pp. 1206-1211, 1985.

[5] X. Chen, A. Lal, M. L. Riccio, and R. F. J. Gilmour, Ultrasonically actuated silicon microprobes for cardiac signal recording," *IEEE Trans. Biomed. Eng.*, vol. 53, no. 8, pp. 1665-1671, 2006.

[6] A. Hennig and H. Elias, "Contributions to the Geometry of Sectioning. VII. Elliptical Cylinders", *Z. Wiss. Mikrosk.*, vol. 66, no. 4, pp. 226-234, December 1964.

[7] F. Piefke, "Chord length distribution of the ellipse", *Lithuanian Mathematical Journal*, vol. 19, no. 3, pp. 325-333, 1979.

We claim:

1. A microprobe comprising:
a probe body formed from silicon and shaped to include a bulk base and a thin probe integral to the bulk base and extending beyond the bulk base, the probe body comprising:
   (a) a core shaped to form the bulk base and the thin probe;
   (b) a lower blade that:
      is integrally formed with the core; and
      terminates in a lower blade pointed tip extending beyond a distal end of the thin probe of the core;
   (c) an upper blade that:
      is formed from silicon nitride deposited on an upper surface of the core opposite the lower blade; and
      terminates in an upper blade pointed tip extending beyond the distal end of the thin probe of the core; and
   (d) a strain gauge that includes two first polysilicon resistors formed in a first region within the bulk base away from the thin probe to have nearly constant resistance values with respect to a strain experienced by the thin probe and two second polysilicon resistors formed in a second region within the bulk base near the thin probe to have resistance values that change with a strain experienced by the thin probe, wherein the first and second polysilicon resistors are connected to form a Wheatstone bridge circuit that measures the strain experienced by the thin probe.

2. The microprobe of claim 1, wherein the first and second polysilicon resistors of the strain gauge are etched on the upper surface.

3. The microprobe of claim 1, wherein the lower blade comprises no strain gauge.

4. The microprobe of claim 1, wherein the upper blade and the lower blade lie on different parallel planes.

5. The microprobe of claim 1, wherein the bulk base tapers along a direction from the bulk base towards the thin probe.

6. The microprobe of claim 5, wherein the bulk base tapers with a catenoid shape.

7. The microprobe of claim 1, further comprising a second thin probe formed in the probe body extending from the bulk base and separate from the thin probe, and a second strain gauge that includes two third polysilicon resistors formed in a third region within the bulk base away from the thin probe to have nearly constant resistance values with respect to a strain experienced by the second thin probe and two fourth polysilicon resistors formed in a fourth region within the bulk base near the second thin probe to have resistance values that change with a strain experienced by the second thin probe, wherein the third and fourth polysilicon resistors are connected to form a second Wheatstone bridge circuit that measures the strain experienced by the second thin probe.

8. The microprobe of claim 1, further comprising a piezoelectric actuator coupled to the microprobe, directly or indirectly, to cause forward-backward movement of the microprobe when actuated.

9. The microprobe of claim 1, wherein the microprobe defines a channel dimensioned for fluid flow.

10. The microprobe of claim 1, wherein the strain gauge is configured to measure a temperature change.

11. The microprobe of claim 1, wherein the strain gauge is configured to measure a biological impedance.

12. The microprobe of claim 1, wherein the strain gauge is configured to measure elasticity of a target in contact with the thin probe.

13. The microprobe of claim 1, comprising:
a piezoelectric actuator coupled to the probe body to actuate the thin probe; and
a feedback coupled to the strain gauge to control the piezoelectric actuator based on output of the strain gauge.

14. The microprobe of claim 1, comprising a mechanism configured to measure a size of a target tissue based on timings of measured events at the thin probe.

15. A microprobe comprising:
a body;
two probe bodies extending from the body, the probe bodies separated from one another by a distance;
two sensors, each sensor coupled to a respective probe body to sense a property of the respective probe body and including two first polysilicon resistors formed in a first region within the body away from the respective probe body to have nearly constant resistance values with respect to a strain experienced by the respective probe body and two second polysilicon resistors formed in a second region within the body near the respective probe body to have resistance values that change with a strain experienced by the respective probe body; and
computational circuitry, responsive to the sensed properties and programmed with instructions to:
recognize a contact event sensed by one of the probe bodies;
recognize common mode noise sensed by the other of the probe bodies; and output an output signal indicative of the contact event minus the common mode noise.

16. The microprobe of claim 15, wherein the probe bodies are separated from one another by a distance of no more than 500 μm.

17. The microprobe of claim 15, wherein the probe bodies are separated from one another by a distance of no more than 1 mm.

18. The microprobe of claim 15, wherein each of the two probe bodies has a tip that includes two separate blades.

19. The microprobe of claim 15, wherein each of the two sensors is configured to measure a temperature change.

20. The microprobe of claim 15, wherein each of the two sensors is configured to measure a biological impedance associated with a respective probe body.

21. The microprobe of claim 15, wherein each of the two sensors is configured to measure elasticity of a target in contact with a respective probe body.

22. The microprobe of claim 15, comprising:
a piezoelectric actuator coupled to the body to actuate the two probe bodies; and
a feedback coupled to the two sensors to control the piezoelectric actuator based on measurements of the two sensors.

23. The microprobe of claim 15, wherein the computational circuitry is configured to measure a size of a target tissue based on timings of measured events from a probe body.

24. The microprobe of claim 23, wherein the computational circuitry is configured to use information from Fast Fourier Transform (FFT) on timings of measured events from the probe body to measure a size of the target tissue.

25. The microprobe of claim 15, wherein each of the probe bodies is structured to include at least one blade for cutting or puncturing a target tissue.

26. The microprobe of claim 15, wherein each of the probe bodies is structured to include two separate blades for cutting or puncturing a target tissue.

27. The microprobe of claim 15, wherein each of the probe bodies is structured to include a conduit to permit suctioning of a target tissue or instillation of a substance into the target tissue.

28. A microprobe, comprising:
a probe body including a bulk base and a thin probe integral to the bulk base and extending beyond the bulk base, the thin probe including a distal end having two blades for interacting with a target tissue;
an ultrasonic actuator coupled to the bulk base to generate an ultrasonic wave to actuate the thin probe in interacting with the target issue;
two first resistors formed in a first region within the bulk base away from the thin probe to have nearly constant resistance values with respect to a strain experienced by the thin probe;
two second resistors formed in a second region within the bulk base near the thin probe to have resistance values that change with a strain experienced by the thin probe; and
a sensor circuit that is connected to the two first resistors and the two second resistors to form a Wheatstone bridge circuit that measures the strain experienced by the thin probe, wherein the sensor circuit is configured to process two events by the two blades of the thin probe to determine a size of a structure in the target tissue.

29. The microprobe of claim 28, wherein:
the probe body includes
a second thin probe extending from the bulk base and separate from the thin probe; and
a second Wheatstone bridge circuit in the sensor circuit, the Wheatstone bridge circuit being formed by (1) two third resistors formed in a third region within the bulk base away from the thin probe to have nearly constant resistance values with respect to a strain experienced by the second thin probe and (2) two fourth resistors formed in a fourth region within the bulk base near the second thin probe to have resistance values that change with a strain experienced by the second thin probe,
wherein the sensor circuit is configured to use outputs of the first and second Wheatstone bridge circuits to eliminate a common mode noise detected by the thin probe and the second thin probe.

30. The microprobe of claim 29, wherein:
the thin probe and the second thin probe are spaced from each other to be sufficiently close to be in a common tissue milieu of the target tissue but far enough apart to minimize touching a common structure within the common tissue milieu.

31. The microprobe of claim 28, comprising:
a feedback coupled to the sensor circuit to control the ultrasonic actuator based on output of the sensor circuit.

* * * * *

UNITED STATES PATENT AND TRADEMARK OFFICE
CERTIFICATE OF CORRECTION

| | | |
|---|---|---|
| PATENT NO. | : 8,197,418 B2 | |
| APPLICATION NO. | : 12/663552 | |
| DATED | : June 12, 2012 | |
| INVENTOR(S) | : Amit Lal et al. | |

It is certified that error appears in the above-identified patent and that said Letters Patent is hereby corrected as shown below:

In Column 1, Line 15, delete "and/or DARPA Grant" and insert -- Grant --, therefor.

In Column 1, Line 54, delete "ϕ=$d_L$," and insert -- σ = $d_L$, --, therefor.

In Column 3, Line 22, delete "(~10KΩ," and insert -- (~10KΩ), --, therefor.

In Column 4, Line 3, delete "100m/s." and insert -- 100μm/s. --, therefor.

In Column 7, Line 25, delete "6° C." and insert -- 60 C --, therefor.

In Column 8, Line 58, delete "varioud" and insert -- various --, therefor.

Signed and Sealed this
Eighteenth Day of December, 2012

David J. Kappos
*Director of the United States Patent and Trademark Office*